United States Patent [19]

Radisch et al.

[11] Patent Number: 5,344,401
[45] Date of Patent: Sep. 6, 1994

[54] CATHETER BALLOON FORMED FROM A POLYMERIC COMPOSITE

[75] Inventors: Herbert R. Radisch; Dennis M. Vigil, both of San Diego, Calif.

[73] Assignee: Interventional Technologies Inc., San Diego, Calif.

[21] Appl. No.: 60,441

[22] Filed: May 12, 1993

Related U.S. Application Data

[62] Division of Ser. No. 811,314, Dec. 20, 1991.

[51] Int. Cl.$^5$ .................. A61M 29/00; A61M 5/32
[52] U.S. Cl. ........................... 604/96; 606/194; 604/265
[58] Field of Search .................. 604/96–103, 604/265; 606/192, 194

[56] References Cited

U.S. PATENT DOCUMENTS

| | | | |
|---|---|---|---|
| Re. 33,561 | 3/1991 | Levy | 604/96 |
| 4,140,126 | 2/1979 | Choudhury | 128/325 |
| 4,141,364 | 2/1979 | Schultze | 128/349 |
| 4,292,974 | 10/1981 | Fogarty et al. | 128/344 |
| 4,406,656 | 9/1983 | Hattler et al. | 604/280 |
| 4,608,984 | 9/1986 | Fogarty | 128/344 |
| 4,702,252 | 10/1987 | Brook et al. | 604/103 X |
| 4,705,517 | 11/1987 | DiPisa, Jr. | 623/12 |
| 4,787,388 | 11/1988 | Hofmann | 128/344 |
| 4,810,543 | 3/1989 | Gould et al. | 604/96 |
| 4,896,669 | 1/1990 | Bhate et al. | 606/194 |
| 4,946,464 | 8/1990 | Peusner | 606/192 |
| 4,950,239 | 8/1990 | Gahara et al. | 604/96 |
| 4,952,357 | 8/1990 | Euteneuer | 604/96 X |
| 4,986,830 | 1/1991 | Owens et al. | 604/96 |
| 5,026,607 | 6/1991 | Kiezulas | 604/96 X |
| 5,035,694 | 7/1991 | Kasprzyk et al. | 606/192 |
| 5,100,381 | 3/1992 | Burns | 604/96 |
| 5,108,415 | 4/1992 | Pinchuk et al. | 604/96 |
| 5,114,423 | 5/1992 | Kasprzyk | 604/96 X |
| 5,179,174 | 1/1993 | Elton | 604/265 |
| 5,195,969 | 3/1993 | Wang et al. | 604/103 X |
| 5,272,012 | 12/1993 | Opolski | 604/96 |

FOREIGN PATENT DOCUMENTS

| | | | |
|---|---|---|---|
| 0214721 | 3/1987 | European Pat. Off. | 604/96 |
| 0274411 | 7/1988 | European Pat. Off. | 604/192 |
| 0303487 | 2/1989 | European Pat. Off. | 604/96 |
| 0457456 | 11/1991 | European Pat. Off. | 604/96 |
| 9208512 | 5/1992 | World Int. Prop. O. | 604/96 |

Primary Examiner—C. Fred Rosenbaum
Assistant Examiner—Frank Wilkens
Attorney, Agent, or Firm—Nydegger & Associates

[57] ABSTRACT

A catheter balloon is provided for medical dilation procedures which is formed from a polymeric composite having an enhanced integrity. The balloon comprises an expandable central body and two tapered termini positioned at opposing ends of the body which are formed from a structural layer of continuous polymeric materials characterized as biaxially oriented in the body, but not in the tapered termini. A layer of an imide-containing polymer is provided external to the structural layer of the tapered termini to coat the termini and strengthen or otherwise enhance the integrity of the termini not having a biaxial orientation. The imide-containing polymer coating may further be continuously extended to the body of the balloon. The imide-containing polymer is applied to the structural layer of the balloon, in a liquid state and heat cured over time to produce a high-integrity coating.

6 Claims, 1 Drawing Sheet

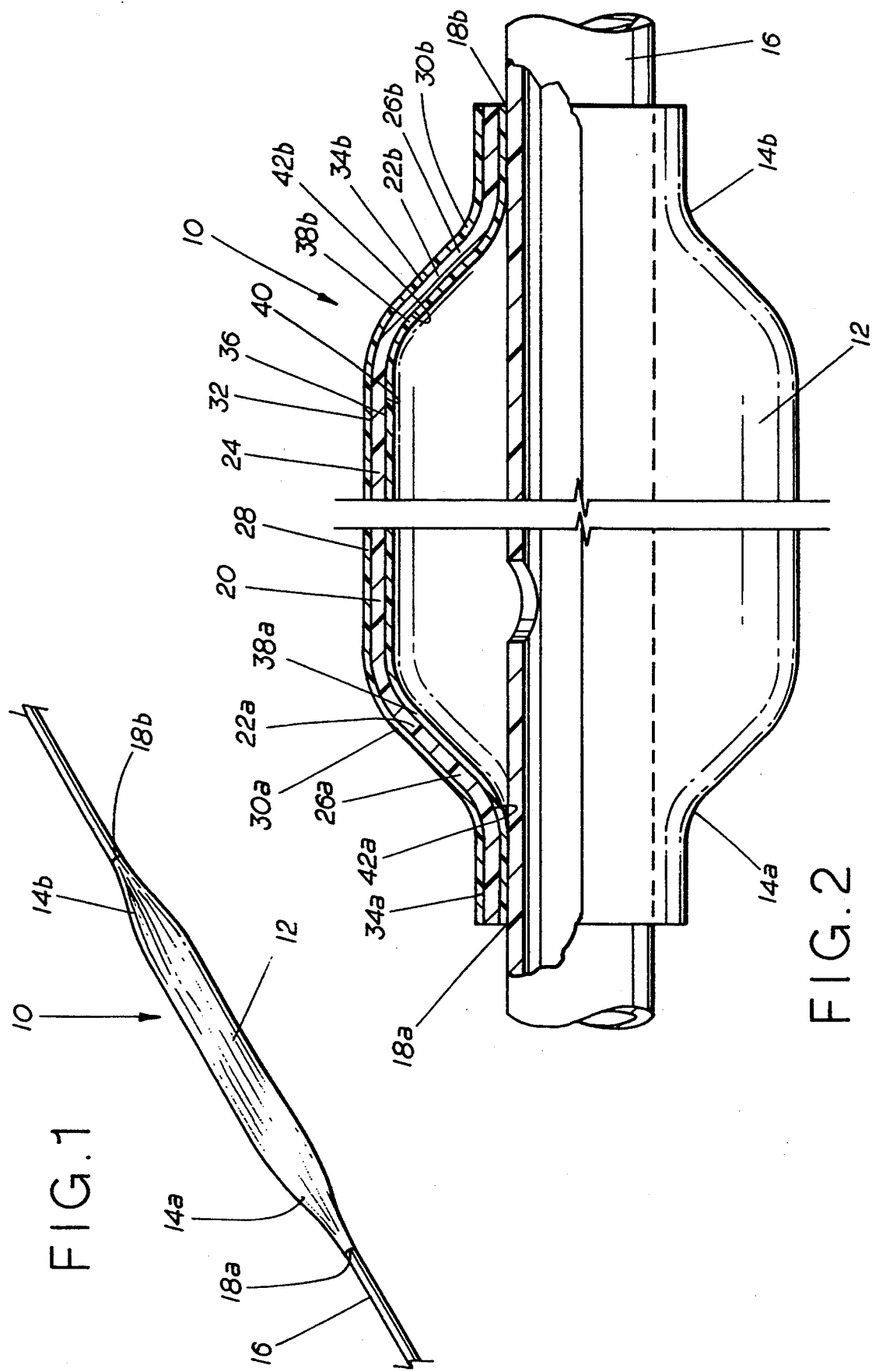

CATHETER BALLOON FORMED FROM A POLYMERIC COMPOSITE

This is a divisional application of U.S. application Ser. No. 07/811 314 filed on Dec. 20 1991.

TECHNICAL FIELD

The present invention relates generally to a catheter balloon for medical dilation procedures and, more particularly, to a catheter-balloon formed from a polymeric composite. The present invention particularly, though not exclusively, relates to a catheter balloon formed from a biaxially oriented polymeric material and a non-biaxially oriented polymeric material having a polymeric coating which enhances the integrity thereof.

BACKGROUND OF THE INVENTION

Use of catheter balloons is widespread in medical dilation procedures. Coronary angioplasty is a typical dilation procedure whereby a catheter having a balloon at its distal end is inserted into a coronary artery exhibiting occlusion. The catheter is positioned such that the balloon is adjacent the occluding stenosis. The balloon is then inflated by injecting a fluid into the balloon via the catheter. The inflated balloon exerts an outward pressure against the stenosis, thereby dilating the artery and alleviating the occlusion.

A critical performance requirement for the balloon is that it have sufficient structural integrity to inflate against the force of the stenosis without rupturing. In many cases the resistive force of the stenosis is substantial and the balloon requires a substantial inflation pressure to overcome this force. It is, thus, apparent that the balloon must be fabricated from a high-integrity material to avoid rupturing while dilating the artery. Consequently, the choice of material from which to fabricate the balloon is critical to the success of the dilation procedure.

Certain high molecular weight polymeric materials have been found to possess the properties necessary to perform as catheter balloons for coronary angioplasty. These properties include thinness, flexibility, and strength. Polymeric materials having a biaxial orientation have been found to be particularly effective because of their high integrity, i.e., high tensile strength and uniformity. Thus, certain biaxially oriented polymers are the material of choice for fabrication of catheter balloons. Manufacture of polymeric materials having a biaxial orientation requires a specific, but well known, molding and stretching process.

Catheter balloons are generally formed in a configuration which fits over a catheter with the catheter passing axially through the balloon. The balloon is tapered at the ends where its walls join the catheter and is wide in the body where its walls radially diverge from the catheter. Unfortunately, it has been found that when polymeric balloons are formed in this configuration, it is virtually impossible to achieve uniform biaxial orientation of the polymer throughout the entire balloon. In particular, it has been found that biaxial orientation of the polymer can be achieved substantially throughout the body of the balloon, but that the tapered ends terminating at the catheter lack biaxial orientation, adopting either a unilateral or random orientation. As a result, the tapered ends of balloons lack the structural integrity of the balloon body and are prone to failure during operation even though the balloons themselves are conventionally termed "biaxially oriented balloons."

In recognition of this problem, a biaxially oriented polymeric balloon is needed having high structural integrity uniformly across the balloon walls including the tapered ends of the balloon. Further, a method is needed whereby the structural integrity of a biaxially oriented polymeric balloon can be enhanced, particularly at the tapered ends of the balloon.

SUMMARY OF THE INVENTION

The present invention is a catheter balloon for medical dilation procedures such as coronary angioplasty. The balloon is formed from a polymeric composite having an enhanced structural integrity. The present invention is additionally a method for enhancing the structural integrity of a biaxially-oriented polymeric catheter balloon. The catheter balloon comprises an expandable central body and two tapered termini positioned at opposing ends of the body to engage the catheter passing axially therethrough. The body and tapered termini are formed from a continuous structural layer of polymeric materials. The materials are characterized as biaxially oriented in the body of the balloon, but not in the tapered termini of the balloon. In a preferred embodiment of the invention, the polymeric materials in the body and the polymeric materials in the termini of the balloon have substantially the same molecular composition, but differ in their orientation.

Since polymeric materials which lack a biaxial orientation are known to be weaker and to generally have less structural integrity than polymeric materials having a biaxial orientation, the present invention provides a layer of an imide-containing polymer or a polyurethane external to the structural layer of the tapered termini to coat the termini and strengthen or otherwise enhance the integrity of the termini. The polymer coating may also be continuously extended to the body of the balloon to further enhance the integrity of the body. The polymer coating may be provided at either or both of the exposed surfaces of the balloon, i.e., at the outer wall, at the inner wall, or at both the inner and outer walls of the balloon.

The method of the present invention comprises applying the polymer coating to the structural layer of the tapered termini, thereby externally coating the termini and strengthening or otherwise enhancing the integrity of that portion of the polymeric balloon which lacks substantial biaxial orientation. The polymer coating may also be applied to the expandable body of the balloon. The polymer coating is preferably applied to the balloon in a liquid state and heat cured over time to produce a high-integrity composite. Application of the polymer coating may be facilitated by first dissolving the polymer in a solvent medium and then applying the entire solution to the structural layer. The solvent is subsequently volatized from the surface of the balloon during curing.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a perspective of the catheter balloon of the present invention; and

FIG. 2 is an enlarged schematic cross-sectional side view of the catheter balloon of the present invention.

DESCRIPTION OF PREFERRED EMBODIMENTS

Referring initially to FIG. 1, a catheter balloon of the present invention, generally designated as 10, is shown having an expandable body 12 and tapered termini 14a, 14b at each end of body 12. FIG. 1 shows body 12 in an expanded state. Balloon 10 is positioned about a catheter 16 passing axially through holes 18a, 18b provided at termini 14a, 14b respectively. A substantially fluid tight seal is provided at holes 18a, 18b where termini 14a, 14b engage catheter 16. The seal may be provided simply by bonding the materials of catheter 16 and balloon 10 or by means of a slip-fit ring clamp (not shown). Balloon 10 and catheter 16 have application to conventional medical dilation procedures known to those skilled in the art, such as coronary angioplasty.

The composite structure of balloon 10 is shown in greater detail with reference to FIG. 2. For purposes of illustration, only the top portion of balloon 10 is shown in cross-section, but it is understood that balloon 10 is symmetrical and that the bottom portion is substantially identical to the top portion. Balloon 10 comprises body 12 having a layered wall 20 and further comprises tapered termini 14a, 14b having layered walls 22a, 22b. Layered walls 20, 22a, 22b form the continuous surface of balloon 10 and are formed generally from a polymeric composite. Internal layer 24 of body 12 and internal layers 26a, 26b of termini 14a, 14b are the structural support for walls 20, 22a, 22b. Structural internal layers 24, 26a, 26b are preferably continuous across walls 20, 22a, 22b.

In the preferred embodiment shown, outer external layer 28 of body 12 and outer external layers 30a, 30b of tapered termini 14a, 14b provide a coating on the outer surfaces 32, 34a, 34b of structural internal layers 24, 26a, 26b respectively. Further, inner external layer 36 of body 12 and inner external layers 38a, 38b of tapered termini 14a, 14b provide a coating on the inner surfaces 40, 42a, 42b of structural internal layers 24, 26a, 26b respectively. Outer external layers 28, 30a, 30b and inner external layers 36, 38a, 38b are preferably continuous across walls 20, 22a, 22b. In other embodiments of the present invention which are not shown, either inner external layers 36, 38a, 38b or outer external layers 28, 30a, 30b may be entirely omitted from balloon 10, although both inner and outer external layers may not be omitted simultaneously. Alternatively, external layers 28 and 36 of body 12 may be omitted from wall 20 leaving structural layer 24 of body 12 exposed and only walls 22a, 22b of termini 14a, 14b with external layers thereon.

In any case, as noted above, internal layers 24, 26a, 26b provide the primary structure of walls 20, 22a, 22b while external layers 28, 30a, 30b, 36, 38a, 38b are a coating thereof. Therefore, the internal layers are preferably thicker than the external layers. External layers have a thickness on the order of between about $5 \times 10^{-5}$ and about $5 \times 10^{-4}$ and preferably between about $1 \times 10^{-4}$ inches and about $3 \times 10^{-4}$ inches, while internal layers have a thickness on the order of between about $1 \times 10^{-4}$ inches and about $8 \times 10^{-4}$ inches and preferably between about $2 \times 10^{-4}$ inches and about $4 \times 10^{-4}$ inches.

Structural layer 24 of body 12 is composed of a biaxially oriented polymer having the molecular composition of polyethylene terephthalate (PET), polyethylene thilate glycolate (PETG), or mixtures thereof. Structural layers 26a, 26b preferably have substantially the same molecular composition as structural layer 24, but layers 26a, 26b are not substantially biaxially oriented. In practice layers 24, 26a, 26b are preferably made from the same starting material, but during the process of biaxially orienting the polymer, the bulk of the polymer in layers 26a, 26b fails to achieve biaxial orientation. Consequently, layers 26a, 26b are characterized as not substantially biaxially oriented. Nevertheless, within the meaning of the term "not substantially biaxially oriented" as used herein, the polymer in layers 26a, 26b may be biaxially oriented to some degree, but to a substantially lesser degree than the polymer in layer 24. The bulk of the polymer in layers 26a, 26b is uniaxially oriented or randomly oriented.

All external layers are preferably uniformly composed of an imide-containing polymer which is most preferably a polyimide. Alternately, the external layers can be composed of a polyurethane. The primary function of the external layers is to enhance the integrity of balloon walls 20, 22a, 22b. It is particularly desirable that the integrity of walls 22a, 22b is enhanced because these walls lack biaxial orientation and inherently have less integrity than wall 20 which is substantially biaxially oriented. The term "integrity" as used herein, refers to the tensile strength and uniformity of balloon walls 20, 22a, 22b. Thus, enhancing the integrity thereof includes strengthening of walls 20, 22a, 22b and curing nonuniformities therein, such as pinhole leaks and the like.

The method of the present invention is performed by coating the desired internal layers of balloon 10 with an imide-containing polymer or a polyurethane to form an enhanced integrity polymeric composite. Preferably, at least the internal layers which are not substantially biaxially oriented, i.e., internal layers 26a, 26b, are coated with the imide-containing polymer according to the present method. The polymer coating is applied to the desired internal layers as a polymeric liquid which is sprayed onto the desired internal layers or into which the balloon 10 is dipped. The polymeric liquid may be a solution of the imide-containing polymer or polyurethane in a solvent medium. A preferred solvent medium includes the solvents, dimethyl pyrrolidine, methylene chloride, acetates, and alcohols, either individually or as cosolvents of one another.

Upon application of the polymer coating to balloon 10 to form the polymeric composite, balloon 10 is cured at a predetermined temperature for a predetermined time as is readily determinable by the skilled artisan. Curing enables the polymer coating to set up on the balloon wall to which it is applied and volatilizes the solvent or solvents, if any are used.

While the particular Catheter Balloon Formed From a Polymeric Composite as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A method for strengthening a portion of a catheter balloon, comprising the steps of:

providing a catheter balloon made from a first polymer, said balloon having a first region of relatively high tensile strength where said first polymer is biaxially oriented, and having a second region of relatively low tensile strength where said first polymer is not biaxally oriented;

applying a liquid coating of a second polymer to a surface of only said second region, said second polymer having a relatively high tensile strength; and raising said balloon and said coating to a sufficiently high temperature to form a high tensile strength composite of said first and second polymers.

2. A method for strengthening a portion of a catheter balloon, as claimed in claim 1, wherein:

said second region has an inner surface and an outer surface; and said step of applying said coating comprises the substeps of applying said coating to both inner and outer surfaces of said second region.

3. A method for strengthening a portion of a catheter balloon, as claimed in claim 1, wherein said second region comprises a tapered end region of said balloon.

4. A method for strengthening a portion of a catheter balloon, as claimed in claim 3, wherein:

said first polymer is selected from the group consisting of PET, PETG, and mixtures thereof; and said second polymer is applied to said surface in the absence of any bond enhancing treatment of said surface.

5. A method for strengthening a portion of a catheter balloon, as claimed in claim 3, wherein said second polymer is selected from the group consisting of polyurethane and imide-containing polymers; and said high tensile strength of said second polymer is preserved by applying said second polymer in the form of a solution comprising said second polymer and a solvent, in the absence of a lubricant.

6. A method for strengthening the tapered ends of a catheter balloon, comprising the steps of:

selecting a first polymer from the group consisting of PET, PETG, and mixtures thereof;

providing a catheter balloon made from said first polymer, said balloon having a body of relatively high tensile strength where said first polymer is biaxially oriented, and having tapered ends of relatively low tensile strength where said first polymer is not biaxally oriented;

providing a second polymer selected from the group consisting of polyurethane and imide-containing polymers, said second polymer being free of added lubricant;

applying a liquid coating of said second polymer to selected surfaces of only said tapered ends, in the absence of any bond enhancing treatment of said selected surfaces; and raising said balloon and said coating to a sufficiently high temperature to form a high tensile strength composite of said first and second polymers at said tapered ends.

* * * * *